US00PP34303P2

(12) United States Plant Patent
Hofmann

(10) Patent No.: US PP34,303 P2
(45) Date of Patent: Jun. 7, 2022

(54) ***LOBULARIA* PLANT NAMED 'INLBUVIOKN'**

(50) Latin Name: *Lobularia maritima*
Varietal Denomination: INLBUVIOKN

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 17/371,645

(22) Filed: Jul. 9, 2021

(51) Int. Cl.
*A01H 6/20* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — C. Anne Whealy

(57) ABSTRACT

A new and distinct cultivar of *Lobularia* plant named 'INLBUVIOKN', characterized by its compact, outwardly spreading, mounding to trailing plant habit; freely branching habit; freely and continuous flowering habit; long flowering period; relatively large purple-colored flowers; tolerance to high temperatures; and good garden performance.

2 Drawing Sheets

Figure 1:
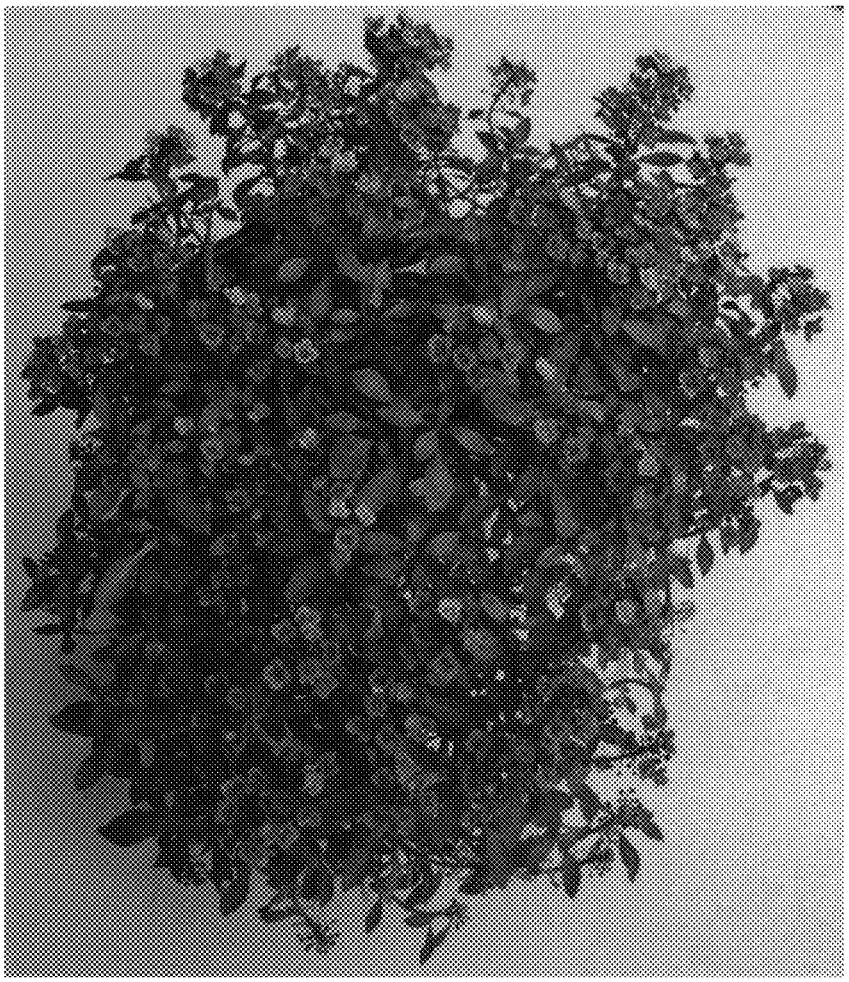

Botanical designation: *Lobularia maritima.*
Cultivar denomination: 'INLBUVIOKN'.

BACKGROUND OF THE INVENTION

The present invention relates to a new and distinct cultivar of *Lobularia* plant, botanically known as *Lobularia maritima*, commonly referred to as Sweet Alyssum and hereinafter referred to by the name 'INLBUVIOKN'.

The new *Lobularia* plant is a product of a planned breeding program conducted by the Inventor in Heidesheim and Gensingen, Germany. The objective of the breeding program was to develop new compact *Lobularia* plants with numerous attractive flowers and long flowering period.

The new *Lobularia* plant originated from an open-pollination during the summer of 2015 in Heidesheim, Germany of a proprietary selection of *Lobularia maritima* identified as code number Lo14-5001-16, not patented, as the female, or seed, parent, with an unknown selection of *Lobularia maritima* as the male, or pollen, parent. The new *Lobularia* plant was discovered and selected by the Inventor as a single flowering plant within the progeny of the stated open-pollination in a controlled greenhouse environment in Heidesheim, Germany in August, 2016. Asexual reproduction of the new *Lobularia* plant by vegetative terminal cuttings in a controlled greenhouse environment in Gensingen, Germany since August, 2016 has shown that the unique features of this new *Lobularia* plant are stable and reproduced true to type in successive generations.

SUMMARY OF THE INVENTION

Plants of the new *Lobularia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INLBUVIOKN'. These characteristics in combination distinguish 'INLBUVIOKN' as anew and distinct *Lobularia* plant:

1. Compact, outwardly spreading, mounding to trailing plant habit.
2. Freely branching habit.
3. Freely and continuous flowering habit.
4. Long flowering period.
5. Relatively large purple-colored flowers.
6. Tolerant to high temperatures and good garden performance.

Plants of the new *Lobularia* differ from plants of the female parent selection in the following characteristics:

1. Plants of the new *Lobularia* flower about two weeks later than plants of the female parent selection.
2. Plants of the new *Lobularia* have larger flowers than plants of the female parent selection.
3. Flowers of plants of the new *Lobularia* are lighter purple in color than flowers of plants of the female parent selection.

Plants of the new *Lobularia* can be compared to (*Lobularia canariensis* x *Lobularia maritima*) X *Lobularia maritima* 'INLOBU1007', disclosed in U.S. Plant Pat. No. 26,931. In side-by-side comparisons, plants of the new *Lobularia* differ from plants of 'INLOBU1007' in the following characteristics:

1. Plants of the new *Lobularia* are more vigorous than plants of 'INLOBU1007'.
2. Plants of the new *Lobularia* have stronger roots than plants of 'INLOBU1007'.
3. Flowers of plants of the new *Lobularia* are lighter purple in color than flowers of plants of 'INLOBU1007'.

Plants of the new *Lobularia* can be compared to *Lobularia maritima* 'Stream Purple', not patented. In side-by-side comparisons, plants of the new *Lobularia* differ from plants of 'Stream Purple' in the following characteristics:

1. Plants of the new *Lobularia* are more vigorous than plants of 'Stream Purple'.
2. Flowers of plants of the new *Lobularia* are lighter purple in color than flowers of plants of 'Stream Purple'.
3. Plants of the new *Lobularia* flower more freely under high temperature conditions than plants of 'Stream Purple'.

BRIEF DESCRIPTION OF THE PHOTOGRAPHS

The accompanying colored photographs illustrate the overall appearance of the new *Lobularia* plant showing the colors as true as it is reasonably possible to obtain in colored reproductions of this type. Colors in the photographs may differ slightly from the color values cited in the detailed botanical description which accurately describe the colors of the new *Lobularia* plant.

The photograph on the first sheet (FIG. 1) is a top perspective view of a typical flowering plant of 'INLBUVIOKN' grown in a container.

Figure 2:
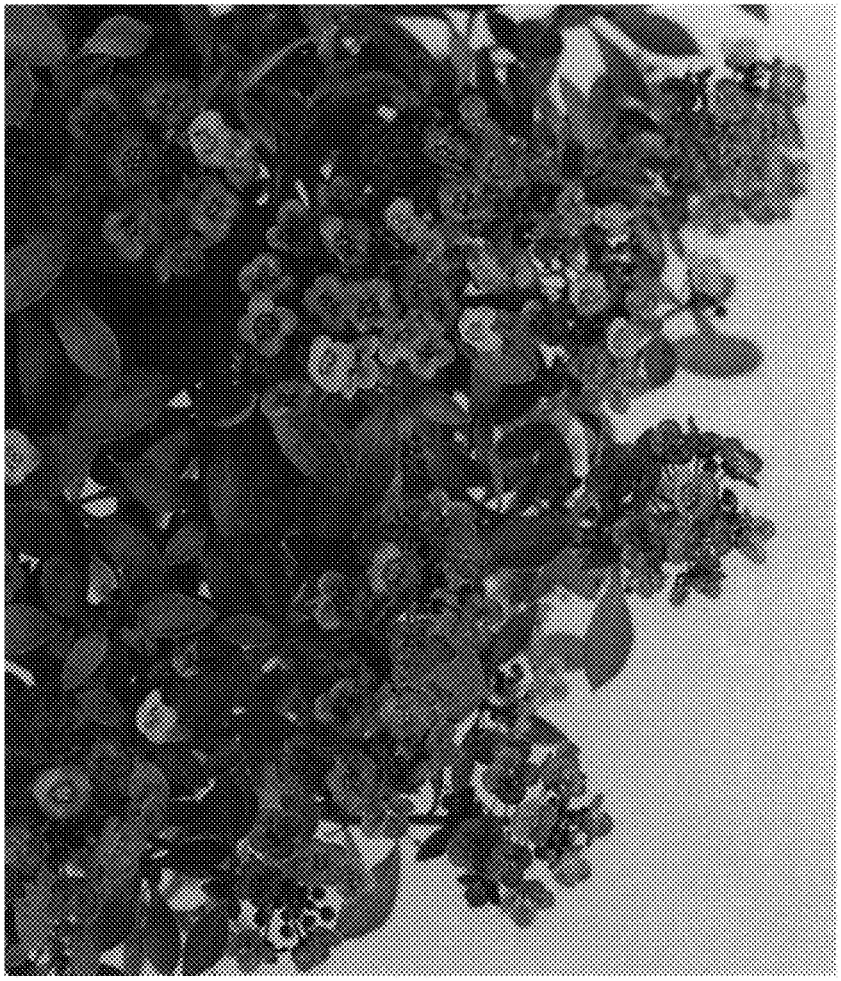

The photograph on the second sheet (FIG. 2) is a close-up view of a typical flowering plant of 'INLBUVIOKN'.

DETAILED BOTANICAL DESCRIPTION

The aforementioned photographs and following observations and measurements describe plants grown during the autumn and winter in 10.8-cm containers in a glass-covered greenhouse in Loudon, N.H. and under cultural practices typical of commercial *Lobularia* production. During the production of the plants, average daily temperatures were 18° C. Plants were grown under long day/short night conditions and were pinched two weeks after planting. Plants were ten weeks from planting when the photographs and description were taken. In the following description, color references are made to The Royal Horticultural Society Colour Chart, 2015 Edition, except where general terms of ordinary dictionary significance are used. Measurements were taken on individual plants.

Botanical classification: *Lobularia maritima* 'INLBUVIOKN'.

Parentage:

*Female, or seed, parent.*—Proprietary selection of *Lobularia maritima* identified as code number Lo14-5001-16, not patented.

*Male, or pollen, parent.*—Unknown selection of *Lobularia maritima*, not patented.

Propagation:

*Type.*—Terminal vegetative cuttings.

*Time to initiate roots, summer.*—About five to seven days at temperatures about 21° C. to 27° C.

*Time to initiate roots, winter.*—About seven to ten days at temperatures about 18° C. to 21° C.

*Time to produce a rooted young plant, summer.*—About three to four weeks at temperatures about 21° C. to 27° C.

*Time to produce a rooted young plant, winter.*—About four to five weeks at temperatures about 16° C. to 18° C.

*Root description.*—Fine, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant form and growth habit.*—Compact, outwardly spreading, mounding and trailing plant habit; freely branching habit with lateral branches potentially developing at every node; dense and bushy appearance; moderately vigorous growth habit and moderate to rapid growth rate.

*Plant height.*—About 8 cm.

*Plant diameter* (*area of spread*).—About 26 cm.

*Lateral branches.*—Length: About 14.5 cm. Diameter: About 2.5 mm. Internode length: About 5 mm to 7.5 mm. Strength: Moderately strong, flexible. Aspect: Upright to outwardly to eventually trailing. Texture and luster: Mostly glabrous with fine and sparse pubescence; longitudinally ridged; moderately glossy. Color: Close to 144A.

Leaf description:

*Arrangement.*—Alternate; simple; sessile.

*Length.*—About 2.25 cm to 2.5 cm.

*Width.*—About 1 cm to 1.25 cm.

*Shape.*—Oblanceolate to elliptic.

*Apex.*—Acute to acuminate.

*Base.*—Cuneate to attenuate.

*Margin.*—Entire, not undulate.

*Texture and luster, upper surface.*—Mostly glabrous with sparse pubescence; slightly to moderately glossy.

*Texture and luster, lower surface.*—Smooth, glabrous; slightly glossy.

*Venation pattern.*—Single midvein discernible.

*Color.*—Developing and fully developed leaves, upper surface: Close to 147A; venation, close to 147A. Developing and fully developed leaves, lower surface: Close to 147A to 147B; venation, close to 147A to 147B.

Flower description:

*Flower type and habit.*—Relatively large rotate flowers arranged in axillary and terminal cymes; flowers face initially upright and mostly outwardly with inflorescence development; freely flowering habit, about 15 to 25 flowers per inflorescence.

*Natural flowering season.*—Relatively long flowering period; plants flower continuously from spring until autumn in New Hampshire.

*Flower longevity on the plant.*—About five to seven days; flowers persistent.

*Fragrance.*—Moderately fragrant; sweet, pleasant.

*Inflorescence height.*—About 1.5 cm to 2 cm.

*Inflorescence diameter.*—About 2 cm to 2.5 cm.

*Flower diameter.*—About 5 mm to 6 mm.

*Flower depth* (*height*).—About 3 mm.

*Flower buds.*—Length: About 2.5 mm. Diameter: About 2 mm. Shape: Roughly spherical to ovoid. Texture and luster: Smooth, glabrous; matte. Color: Sepals, close to 144A; distally tinged with close to N187A.

*Petals.*—Quantity and arrangement: Four petals arranged in a single whorl. Lobe length: About 2.5 mm to 3 mm. Lobe width: About 2.5 mm to 3 mm. Shape: Spatulate. Apex: Obtuse. Base: Attenuate with a short stalk; stalk is 1 mm to 1.5 mm. in length and 0.5 mm in diameter. Margin: Entire, not undulate. Texture and luster, upper and lower surfaces:

Smooth, glabrous; velvety; matte. Color: When opening and fully opened, upper surface: Close to between N78A and N81A; venation, between N78A and N81A; color becoming closer to N81B, N81C and N81D with subsequent development. When opening and fully opened, lower surface: Close to 77A; venation, 77A; color becoming closer to 77B to 77C with subsequent development.

*Sepals.*—Quantity and arrangement: Four sepals arranged in a single whorl; calyx, cruciform. Length: About 1.5 mm to 2 mm. Width: About 1 mm. Shape: Lanceolate. Apex: Acute to acuminate. Base: Fused at the base. Margin: Entire. Texture and luster, upper surface: Smooth, glabrous; matte. Texture and luster, lower surface: Slightly pubescent; matte. Color, upper and lower surfaces: Close to 144A tinged with close to N187A.

*Peduncles.*—Length: About 1.25 cm to 2 cm. Width: About 2 mm. Strength: Moderately strong, wiry and flexible. Aspect: Upright to slightly outwardly. Texture and luster: Fine and sparse pubescence; longitudinally ridged; slightly glossy. Color: Close to 144A.

*Pedicels.*—Length: About 3 mm to 5 mm. Width: About 1 mm. Strength: Moderately strong, wiry and flexible. Aspect: Initially upright to almost horizontal depending on position of the flower on the inflorescence. Texture and luster: Fine and sparse pubescence; longitudinally ridged; slightly glossy. Color: Close to 144A.

*Reproductive organs.*—Stamens: Quantity per flower: Four. Filament length: About 1.5 mm. Filament color: Close to 144A to 144B. Anther shape: Oblong. Anther size: About 0.5 mm by 1 mm. Anther color: Close to 9A. Pollen amount: None observed. Pistils: Quantity per flower: One. Pistil length: About 2 mm. Style length: About 1.75 mm. Style color: Close to 144A. Stigma shape: Rounded. Stigma color: Close to 144A to 144B. Ovary color: Close to 144A to 144B.

*Seeds and fruits.*—To date, seed and fruit production have not been observed on plants of the new *Lobularia*.

Pathogen & pest resistance: To date, plants of the new *Lobularia* have not been noted to be resistant to pathogens or pests common to *Lobularia* plants.

Garden performance: Plants of the new *Lobularia* have been observed to have good garden performance and to tolerate temperatures ranging from about 4° C. to about 35° C.

It is claimed:

1. A new and distinct *Lobularia* plant named 'INLBUVIOKN' as illustrated and described.

* * * * *